(12) United States Patent
Gardeski et al.

(10) Patent No.: US 7,029,460 B2
(45) Date of Patent: Apr. 18, 2006

(54) SLITTING TOOL

(75) Inventors: Kenneth C. Gardeski, Plymouth, MN (US); Stanten C. Spear, Arden Hills, MN (US); Andrzej M. Malewicz, Minneapolis, MN (US); Jeremy J. Odegard, River Falls, WI (US)

(73) Assignee: Medtronic, Inc., Minneapolis, MN (US)

( * ) Notice: Subject to any disclaimer, the term of this patent is extended or adjusted under 35 U.S.C. 154(b) by 405 days.

(21) Appl. No.: 10/078,026

(22) Filed: Feb. 15, 2002

(65) Prior Publication Data

US 2003/0158565 A1    Aug. 21, 2003

(51) Int. Cl.
*A61M 5/178*    (2006.01)

(52) U.S. Cl. .................................... 604/160
(58) Field of Classification Search ........... 604/164, 604/160, 161, 524, 95, 264, 526, 527, 523; 606/191, 192–197
See application file for complete search history.

(56) References Cited

U.S. PATENT DOCUMENTS

| | | |
|---|---|---|
| 2,141,002 A | 12/1938 | Huff |
| 2,616,172 A | 11/1952 | Parker |
| 3,831,274 A | 8/1974 | Horrocks |
| 3,902,501 A | 9/1975 | Citron et al. |
| 4,394,828 A | 7/1983 | Garbis et al. |
| 4,631,059 A | 12/1986 | Wolvek et al. |
| 4,687,469 A * | 8/1987 | Osypka ............... 604/161 |
| 4,997,424 A | 3/1991 | Little |
| 5,188,606 A | 2/1993 | Maloney et al. |
| 5,261,887 A | 11/1993 | Walker |
| 5,322,513 A | 6/1994 | Walker |
| 5,330,460 A * | 7/1994 | Moss et al. ............ 30/90.4 |
| 5,409,469 A | 4/1995 | Schaerf |
| 6,159,198 A | 12/2000 | Gardeski et al. |
| 6,280,433 B1 | 8/2001 | McIvor et al. |
| 6,497,681 B1 * | 12/2002 | Brenner ............. 604/164.05 |

FOREIGN PATENT DOCUMENTS

| | | |
|---|---|---|
| DE | 343987 | 1/1960 |
| EP | 0391544 | 10/1990 |

* cited by examiner

*Primary Examiner*—Vy Bui
(74) *Attorney, Agent, or Firm*—Michael C. Soldner; Girma Wolde-Michael

(57) ABSTRACT

A slitting tool is provided for severing a tubular body such as the body of an introducer or a guide catheter that is positioned around an implantable medical device (IMD) such as a lead or another catheter. The slitting tool includes a body member that has a surface adapted to be gripped by a user. The surface includes a channel that is provided to align the IMD with respect to the body of the slitting tool. The gripping action of the user maintains the IMD within the channel such that the channel need not attach to the IMD. The slitting tool includes a cutting member coupled to the body member and positioned to sever the tubular body without severing the IMD.

23 Claims, 7 Drawing Sheets

SLITTING TOOL

FIELD OF THE INVENTION

The current invention relates to an improved tool for slitting a catheter or introducer; and more particularly, relates to a slitting tool that is easier and more comfortable to use.

BACKGROUND OF THE INVENTION

Catheters and medical electrical leads are often inserted into a patient's body by means of introducer systems. These introducer systems typically include an elongated sheath which is inserted into the blood vessel or other portion of the patient's body. A catheter or lead may then be introduced through a lumen of the introducer. In those circumstances in which the lead or catheter is to remain in the patient's body for a considerable period of time, it is desirable to be able to remove the introducer sheath without removing the lead or catheter.

Another related procedure involves placing a lead at a target destination through a lumen of a guide catheter. After the lead is in position, the guide catheter must be removed from the body while leaving the lead undisturbed. If the lead is coupled to an isodiametric connector that is substantially the same size as the lead body, the guide catheter can be removed from the body by pulling the guide catheter over the connector. Many connectors, however, are larger than the lead body so that the guide catheter cannot be withdrawn over the connector, and some other means of removal must be employed.

One commonly employed mechanism for removing an introducer sheath or a guide catheter from around another device is to provide the sheath or guide catheter with weakened zones so that it can be torn or split and thereby removed from around the encircled device. One introducer system employing this mechanism is illustrated in U.S. Pat. No. 5,409,469 issued to Scheaerf, incorporated herein by reference in its entirety.

Another commonly employed mechanism for removing a sheath or guide catheter from around a catheter or lead is to simply slit the sheath along its length as it is pulled proximally along the inner lead or catheter and out of the patient's body. Various exemplary slitter designs are disclosed in U.S. Pat. No. 4,997,424 issued to Little, U.S. Pat. No. 6,159,198 issued to Gardeski, and U.S. Pat. No. 5,330,460 to Moss et al. These prior art designs include mechanisms that grasp or otherwise couple to a lead or catheter body. For example, the '424 patent to Little describes a slitter that includes an arcuate section having an inner peripheral wall that extends arcuately through an angle of at least about 180 degrees, and which is adapted to abut against a catheter while an introducer tube is slit away from the catheter body.

Because prior art slitter tools are adapted to couple to the inner lead or catheter body while the encircling introducer or guide catheter is being slit away, the dimensions of the slitter tool must be tailored for a particular lead or catheter. For example, a slitting tool adapted to couple to a 4 French lead will not properly attach to a 2 French lead, and so on. As a result, pre-packaged lead, catheter, or introducer kits must be provided with specific slitting tools sized for use with the devices in the kit. This increases manufacturing costs.

Another problem associated with the coupling mechanisms of prior art slitting tools involves difficulties with deployment. Prior art clamping mechanisms add unnecessary bulk and complexity to the slitter. Moreover, such tools may attach to a lead body in a manner that is not intuitive. As a result, the user may incorrectly couple the slitter to the lead body, and the outer surface of the lead may therefore be damaged during the slitting process.

Yet another difficulty with using prior art slitting tools has to do with lead dislodgement. The coupling mechanisms provided by prior art slitting tools could suddenly disengage from a lead during the slitting process. This may cause the lead body to abruptly move in a manner that dislodges the lead distal tip. As a result, the lead placement procedure must be repeated, resulting in additional trauma to the patient.

Another disadvantage with prior art slitting tools is that they are not designed ergonomically. For example, most prior art tools are adapted to be grasped by the user with the index finger and thumb in the general plane of the cutting blade. In this case, the reactionary force causing by the slitting process is resisted by squeezing the slitter between the index finger and the thumb, which does not provide good support. Moreover, many tools of this type require the palm of the hand to be generally facing in an upward direction, which tends to be unstable. Finally, grasping a slitting tool in this manner encourages the user to incorrectly push the slitter toward the catheter rather than to pull the catheter past the slitter in the correct manner of use. As a result, the slitting process is made much more difficult, and potential damage to the inner device may occur.

What is needed, therefore, is an improved slitting tool that addresses the forgoing problems.

SUMMARY OF THE INVENTION

An improved slitting tool is provided for severing a tubular body such as the body of an introducer or a guide catheter that is positioned around an implantable medical device (IMD) such as a lead or another catheter. The slitting tool includes a body member that has a surface adapted to be gripped by a user. The surface includes a channel that is provided to align the IMD with respect to the body of the slitting tool. The gripping action of the user maintains the IMD within the channel such that the channel need not attach to the IMD. The slitting tool includes a cutting member coupled to the body member and positioned to sever the tubular body without severing the IMD. The cutting member of one embodiment has a blade angle of less than sixty degrees with respect to the tubular body being slit. In another embodiment, the cutting member has a sawtooth edge to aid in cutting through a hub of an introducer or guide catheter.

In one embodiment, the gripping surface has a recessed area that may be textured, and is further adapted for receiving a thumb of the user. According to another aspect of the invention, at least a portion of the channel may be formed within an overmold area that is provided adjacent to a base area. The overmold area may be formed of a lower durometer polymer than that forming the base portion of the body member. A polymer is selected that will provide a tacky surface within the channel to further aid in retaining the IMD during the slitting procedure.

In another embodiment, the slitting tool may include a gripping member such as a ring to receive at least one finger of a user. This gripping member provides enhanced stability and control during the slitting procedure. A nose portion may also be provided to enhance control. The nose portion, which may project from the body, is adapted to provide at least a portion of channel, and may be positioned between the IMD and the tubular body to protect the IMD during the slitting process.

The slitting tool of the current invention may be used with IMDs of various sizes since the channel is not sized to couple to a particular device. Moreover, the channel provides an intuitive mechanism for aligning the IMD that substantially prevents misuse of the tool. The tool is also adapted to be ergonomic, since the tool may be grasped with the hand and wrist in a natural position that promotes control during the slitting operation.

DETAILED DESCRIPTION OF THE INVENTION

Figure 1:
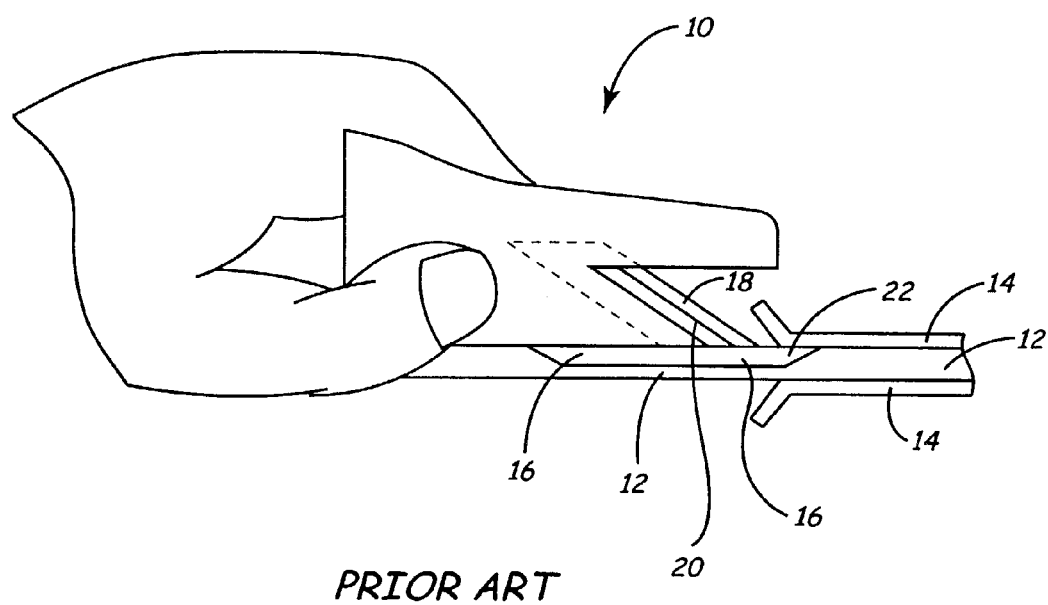
FIG. 1 is a side view of a prior art slitting tool coupled to a catheter positioned within an introducer.

FIG. 1 is a side view of a prior art slitting tool 10. The slitting tool, which is similar to that described in U.S. Pat. No. 4,997,424 to Little, includes an arcuate section 16 adapted to engage with, and couple to, the curved outer surface of a catheter 12. Slitting tool 10 further includes a blade 18 fastened to front edge 20.

Catheter 12 of FIG. 1 may be an IMD including one or more pacing electrodes adapted to be implanted within a heart or elsewhere in the body. This type of IMD may be positioned within the body using an introducer such as introducer 14. After the positioning operation is complete, the introducer must be removed from the body while leaving the IMD in position. This may be accomplished using the prior art slitting tool of FIG. 1. During the slitting operation, the slitting tool is fastened to the proximal end of catheter 12 in the manner shown. Introducer 14 is then pulled toward blade 18 of slitting tool 10. Nose 22 of arcuate section 16 slides under introducer 14, which is slit by blade 18. Rear portion 24 of slitting tool may be gripped by the user as shown during this procedure.

As shown in FIG. 1, the prior art tool is adapted to be grasped with the thumb and index finger in the general plane of the blade. This requires the user to rotate the wrist in an unnatural position that challenges the user's coordination and strength during the slitting operation. The current invention addresses this limitation of the prior art system in a manner to be discussed below.

Figure 2:
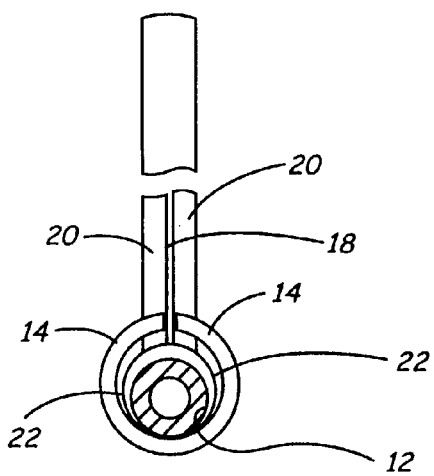
FIG. 2 is a cross-sectional view of the prior art slitting tool of FIG. 1 illustrating the slitting of the introducer.

FIG. 2 is a cross-sectional view of prior art slitting tool 10 as introducer is being slit. This view shows nose 22 of arcuate section 16 coupled to catheter 12. Blade 18 is cutting through introducer 14 as introducer is pulled in a proximal direction across the blade.

Figure 3:
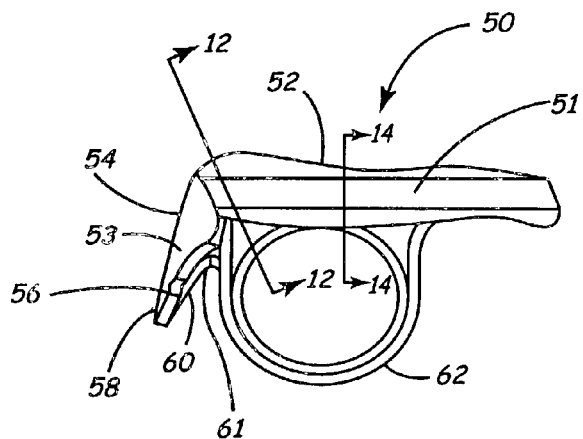
FIG. 3 is a side plan view of one embodiment of a slitting tool according to the current invention.

FIG. 3 is a side plan view of one embodiment of a slitting tool 50 according to the current invention. This embodiment includes a body 51 having a top surface 52. Body 51 is coupled to a nose section 53. Nose section has a front surface 54, and an inner surface 56. Front surface 54 and inner surface 56 intersection at a tip portion 58. Inner surface 56 is coupled to a cutting member 60 such as a blade. Body 51 of the current embodiment includes a ring-like gripping member 62 to aid in grasping slitting tool 50, and to protect the fingers from cutting member 60. Any other shape or size gripping mechanism may be utilized in the alternative, and the ring is merely exemplary.

As shown in FIG. 3, the cutting member 60 of one embodiment has a shallow angle of between 15 and 45 degrees with respect to the tubular body being slit. In a particular embodiment, the cutting member has a blade angle of approximately 30 degrees when measured from the front surface. This angle is more shallow than in prior art cutting tools generally having blades angled at 60 degrees or more. A more shallow angle results in a smoother cutting action with an approximately ten percent lower slitting force.

It may further be noted that the cutting member 60 shown in FIG. 3 has a curved cutting edge portion 61 with a sawtooth configuration. This portion of the blade is particularly effective in cutting through a slittable hub located at the proximal end of many guide catheters. The apex of the blade is shaped to receive the conical taper of the hub and to stabilize the slitter prior to, and during, the hub slitting process. The apex of the blade can be further optimized in shape and position to slit the shaft of introducer sheaths and catheters. In this latter case, the apex is more pointed and moved distal toward the tip portion 58 and closer to the front surface.

Figure 4A:
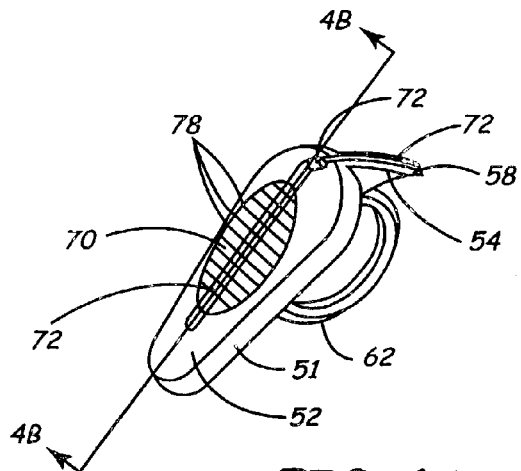
FIG. 4A is a top perspective view of the slitting tool of FIG. 3.

FIG. 4A is a top perspective view of slitting tool 50. This view shows a recessed area 70 on top surface 52. Recessed area is adapted to receive a thumb of either hand when slitting tool 50 is being grasped by a user during a slitting operation. It may be noted that in another embodiment wherein the orientation of recessed area is changed within respect to the body of the slitting tool, recessed area could be adapted to receive a finger other than the thumb. This recessed area may have textured ridges 78 of any other type of texturing in the manner shown to allow for an enhanced grip. For example, texturing could be provided by surface treating recessed area 70 using a plasma etching, chemical milling, or ion bombardment process.

Top surface 52 further includes a channel 72 that extends along at least a portion of top surface, and further continues along at least a portion of front surface 54 of nose section 53. In the embodiment shown, channel 72 runs the entire length of nose section 53 to tip portion 58. This channel is provided to align a lead, catheter, or body of another implantable device in relation to the guide catheter and slitter, but does not clamp or affix to the lead. The lead is instead held in place by the user's thumb positioned within recessed area in a manner to be discussed further below. Channel 72 may be semi-circular, may form a "V" or a "U", may have a stepped surface, or may be formed in another shape. In addition, the surface of channel 72 may be textured or smooth. Texturing may be provided using any means known in the art, including those discussed in the foregoing paragraph. Providing channel 72 with a textured surface helps to prevent relative movement of a lead, catheter, or other IMD in relation to the slitting tool without the use of a clamping or affixing mechanism. In one embodiment, channel 72 extends through an angle of less than 180 degrees. In a particular embodiment, the channel ranges from 40 to 160 degrees.

Figure 4B:
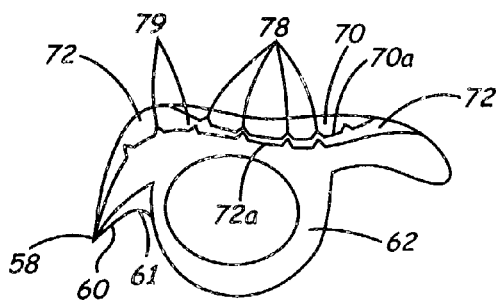
FIG. 4B is a cross-sectional view along line 4B—4B of FIG. 4A.

FIG. 4B is a cross-sectional view of slitting tool 50 along line 4B—4B of FIG. 4A. This view illustrates an embodiment wherein the bottom surface 72a of channel 72 includes texturing 79 in the manner discussed above. Bottom surface 70a of recessed area 70 also includes texturing 78.

Figure 5:
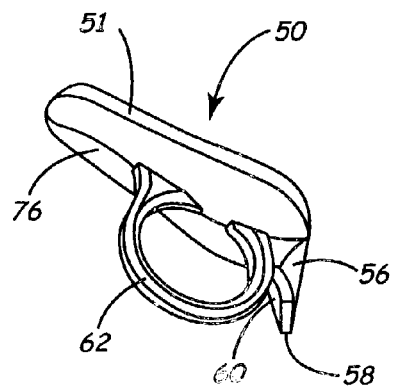
FIG. 5 is a bottom perspective view of the slitting tool of FIG. 3.

FIG. 5 is a bottom perspective view of slitting tool 50. This view further illustrates gripping member 62, and a bottom surface 76 of slitting tool.

Figure 6:
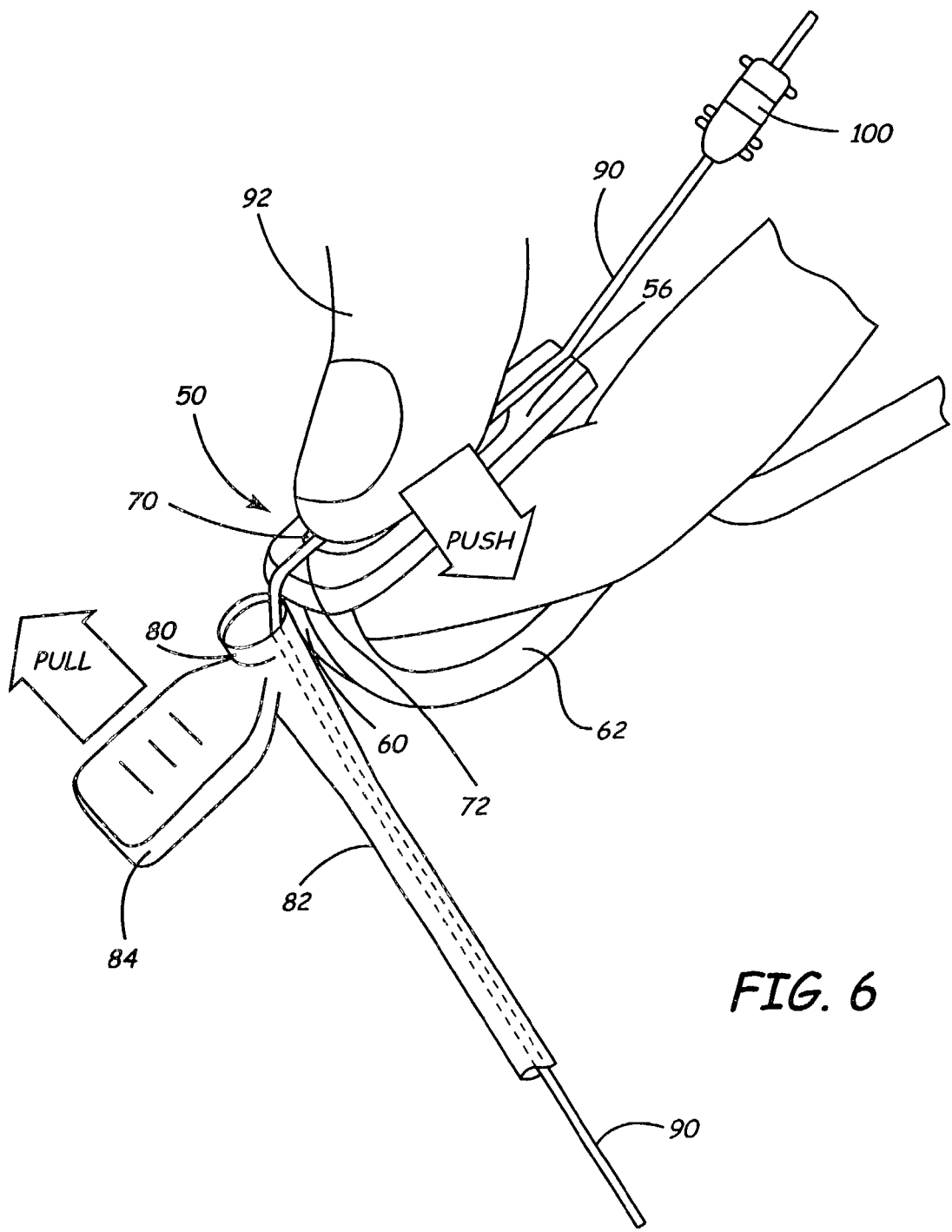
FIG. 6 is a perspective side view of the slitting tool of FIG. 3 engaging a hub of a guide catheter.

FIG. 6 is a perspective side view of slitting tool 50 engaging a hub 80 of a guide catheter 82. Only a proximal portion of guide catheter 82 is shown. A lead 90 (shown partially dashed) is positioned within an inner lumen of guide catheter 82, with a proximal end extending beyond proximal end of the guide catheter. The proximal portion of the lead is positioned within channel 72. Because of the size of the channel, only a portion of the lead 90 resides within channel 72. A thumb 92 of user may be placed over the lead, with pressure applied in a downward direction. This force maintains lead 90 against top surface 52 within recessed area 70.

In one embodiment of the invention, channel 72 is deeper at the top of nose section 53 where top surface 52 and front surface 54 intersect. In this region, channel 72 may be deep enough to receive the entire body of the lead 90. This protects lead 90 from the sharp slit edge of the catheter during the slitting process. This deeper portion of the channel also helps retain the lead prior to positioning a finger within recessed area.

Slitting tool 50 is used by pulling a handle 84 of guide catheter 82 toward the user and over cutting member 60. Severing guide catheter 82 in this manner allows the catheter to be removed from around lead 90, since connector assembly 100 is too large to allow catheter to be retracted over the connector. Channel 72 in the top of nose section 53 supports lead 90 and redirects it so that it does not contact a sharp severed edge of guide catheter 82. This portion of channel 72, transitioning from nose section 53 to top surface 52, is typically constructed deeper to protect the lead from being damaged during the slitting operation. This view further shows the manner in which a pushing force applied by the hand gripping slitting tool will be opposed by an opposite pulling force asserted by another hand that is gripping hub 80 of guide catheter 82.

Figure 7:
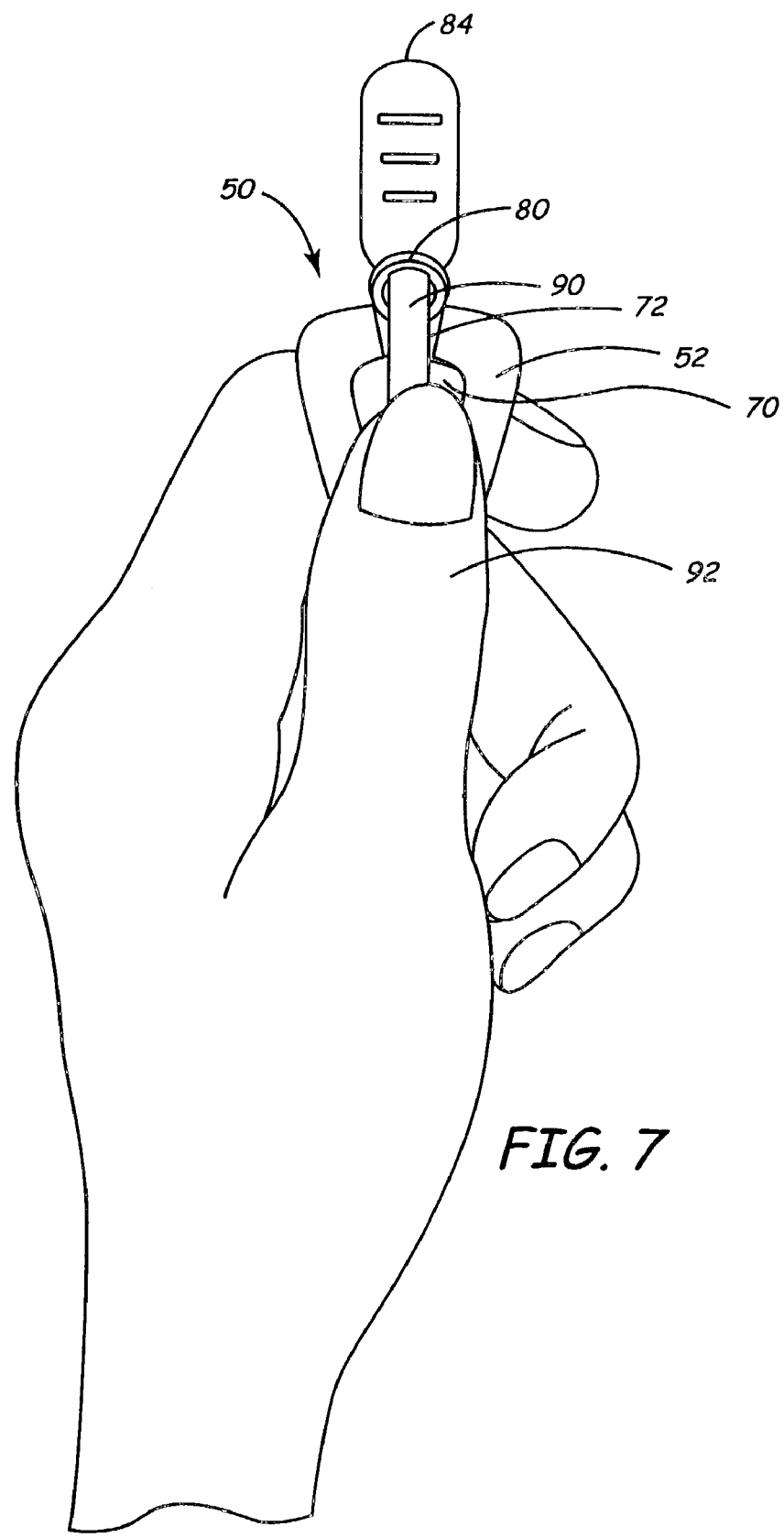
FIG. 7 is a top view of the slitting tool of FIG. 3 illustrating one manner of use.

FIG. 7 is a top view of slitting tool 50 illustrating one manner of using the tool. A portion of lead 90 is positioned within channel 72, which is shown extending into recessed area 70 of top surface 52. Thumb 92 of user is positioned over recessed area 70 and channel 72 to hold lead 90 in position. This view further illustrates that cutting tool may be gasped with the palm of the user's hand facing inward toward the user's body and a slightly downward direction. Moreover, the current tool need not be grasped with the thumb and forefinger positioned within the general plane of the cutting blade. This is a more comfortable orientation than prior art designs. Additionally, the manner of grasping the tool provides for better stability and user control.

Figure 8:
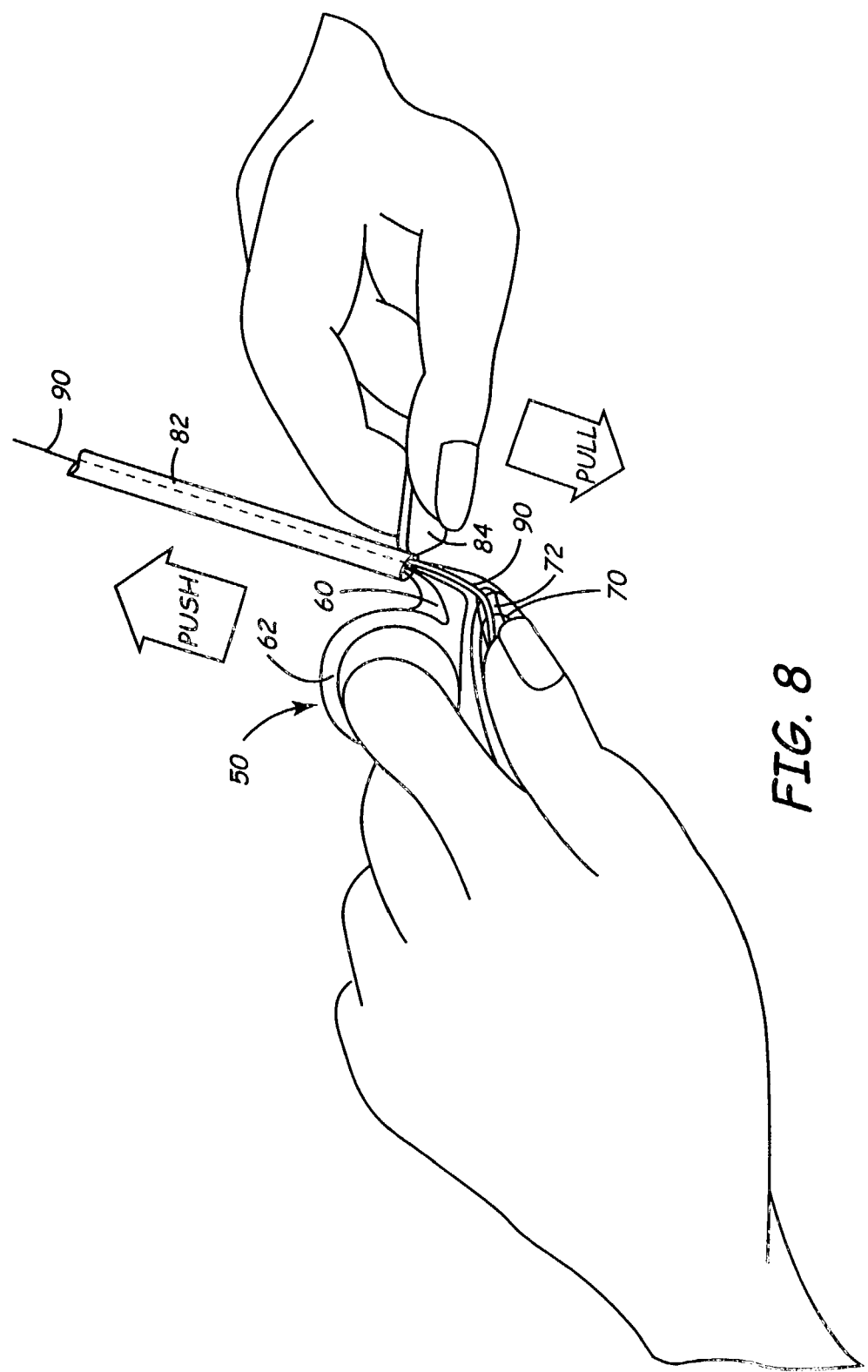
FIG. 8 is a side view of the slitting tool of FIG. 3 illustrating another manner of use.

FIG. 8 is a side view of slitting tool 50 illustrating another manner of use. This figure illustrates the manner in which the hand gripping the slitting tool asserts a pushing force that is opposed by the other hand gripping a handle 84 of the guide catheter 82. In this view, the user performs slitting action with the palm of the hand facing in a generally downward direction. The current invention may be used in this manner or in the manner discussed above based on user preference, patient orientation, and user characteristics which may include the user's height. Further, slitting tool may be used by either a left or right hand. Finally, one skilled in the art will appreciate that slitting tool may be adapted for use with a finger other than a thumb by positioning recessed area and channel on another surface of the slitting tool 50.

Figure 9:
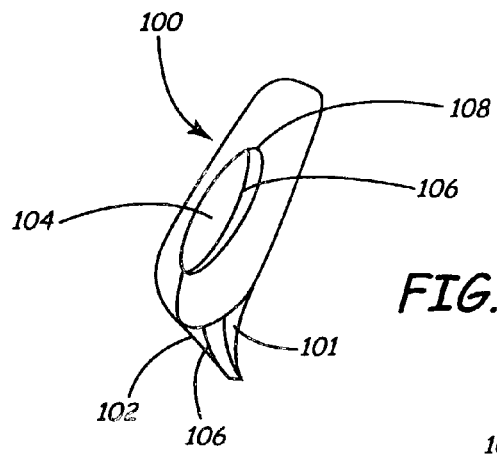
FIG. 9 is a top perspective view of another embodiment of the inventive slitting tool.

FIG. 9 is a top perspective view of another embodiment of the current invention. According to this embodiment, slitting tool 100 does not include gripping member 62 (FIGS. 1–8), and nose portion 102 is shorter than illustrated in previous embodiments. Slitting tool 100 includes a cutting member 101, a recessed area 104, and a channel 106, all of which are similar to aspects of the previous embodiment discussed above. In the current embodiment, channel 106 extends over a portion of top surface 108 and over the entire length nose portion 102.

Figure 10:
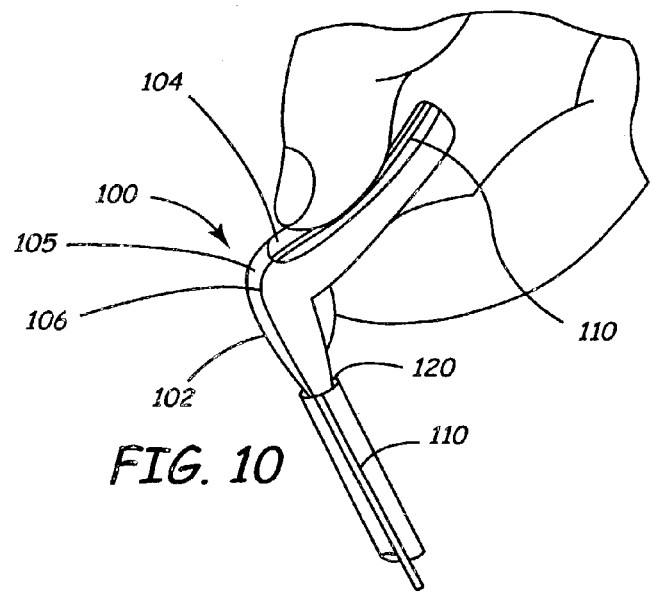
FIG. 10 is a side perspective view illustrating a manner of using the slitting tool of FIG. 9.

FIG. 10 illustrates a manner of using slitting tool 100. Thumb of user is positioned within recessed area 104, and holds a lead 110 in position within channel 106. Nose portion 102 is shown extending into catheter 120 (shown cutaway), with nose portion 102 supporting lead 110 in preparation for slitting the catheter. In this embodiment, channel has a maximum depth around top 105 of nose portion 102 such that lead 110 is barely visible in this region. This embodiment helps protect the lead in a manner discussed above.

Figure 11:
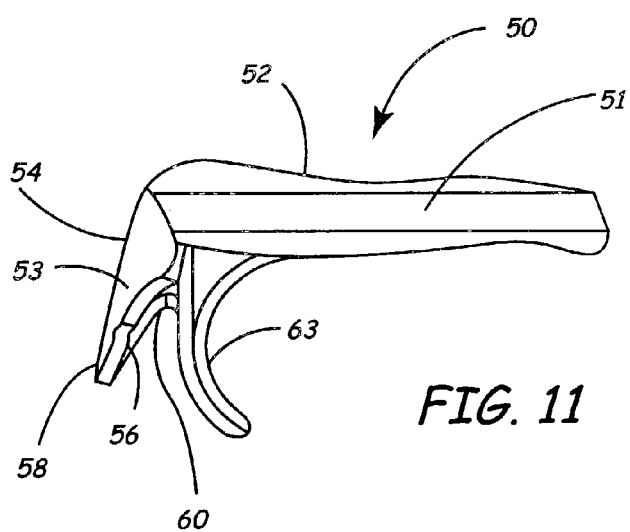
FIG. 11 is yet another embodiment of the current invention providing a guard member to protect the user from cutting member.

FIG. 11 is yet another embodiment of the current invention providing a guard member 63 to protect the user against cutting member 60. Other aspects of this embodiment similar to those shown in FIG. 3 are labeled with like numeric designators. Guard member 63 prevents fingers of a user from sliding forward and contacting cutting member 60. In one embodiment, guard member 63 may be a partial ring similar in shape and structure to gripping member 62 (FIG. 3.) In another embodiment, guard member 63 may take a different shape and/or size.

Many alternative embodiments of the current invention may be contemplated by one skilled in the art. For example, channel 72 may take any desired shape such as a generally "V" shaped channel, a "U" channel, a "stepped-V" or "stepped-U" channel, a combination thereof, or any other desired shape. The channel may extend over a portion, or all, of front surface 54 of nose section 53, and may extend over a portion, or all, of top surface 52. Channel may have a uniform shape, width and depth, or a shape and/or size that varies along the channel length. For example, the depth of channel may be at a maximum at the intersection of top surface 52 and front surface 54 in the manner discussed above. At this location, the shape may be a relatively deep "V" shape, with a more shallow rounded channel used elsewhere. Similarly, recessed area 70 may take many shapes and sizes, included stepped, rounded, or "V-shape"

surfaces, as noted above. Such constructions allow one slitting tool with one blade to accommodate several lead body diameters.

According to one aspect of the invention, a tacky overmolding material formed of a relatively low durometer polymer may be used to form all, or a portion, of the channel. A tacky channel surface minimizes relative movement of the slitting tool to the axis of the lead body or catheter. In one exemplary embodiment, an aromatic polyurethane such as Thermedics Tecothane® TT-1074A, 75 Shore A durometer may be overlaid over a more rigid polyurethane such as DOW Isoplast™ 301 or DOW Pellethane® 2363-75D, which is used to form the body of the slitting tool. Texturing may be provided in the overmold surface, if desired.

Figure 12:
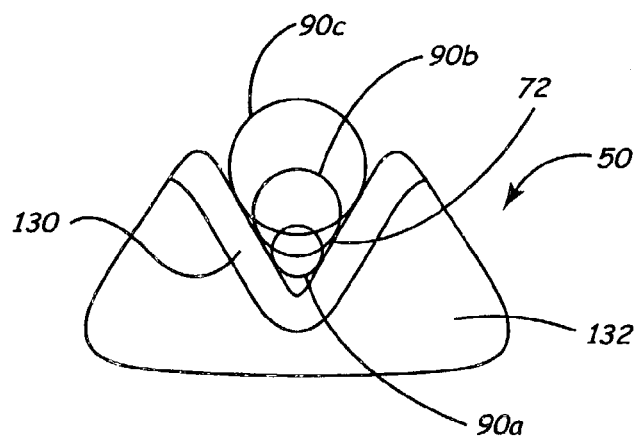
FIG. 12 is a cross-sectional view of the slitting tool of FIG. 3 along line 12—12.

FIG. 12 is a cross-sectional view of slitting tool 50 at line 12—12 of FIG. 3. As noted above, channel 72 may be of a non-uniform depth, and in one preferred embodiment, has a depth that is at a maximum at the intersection of top surface 52 and front surface 54 at the location roughly shown by line 12—12. In this embodiment, channel 72 is generally shaped as a "V", although a "U" or other type shape may be selected in the alternative. This view shows an optional overmolded area 130 that includes channel 72. The overmolding may be formed of the lower durometer, tacky polymer that adheres to the lead body, as described above. A harder material may be used to form the body 132 of the slitter. FIG. 12 illustrates the manner in which IMDs such as leads 90a, 90b, and 90c having varying diameters may be accommodated by the channel. In a preferred embodiment, the current invention accommodates IMDs having a diameter of between 2 and 8 French.

Figure 13:
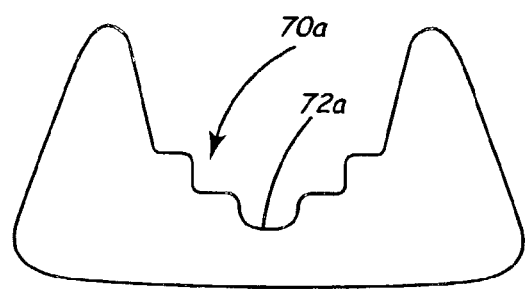
FIG. 13 is a cross-sectional view of another embodiment of the slitting tool at line 12—12 of FIG. 3.

FIG. 13 is a cross-sectional view of another embodiment of slitting tool 50 at line 12—12 of FIG. 3. In this embodiment, recessed area 70a is formed by a series of rounded steps designed to accommodate various lead and/or catheter body dimensions in a manner similar to that shown in FIG. 12. Channel 72a is a "U-shaped" groove at the bottom of recessed area. Although not shown, an overmolded area may be incorporated into the slitter in the manner discussed in reference to FIG. 12.

Figure 14:
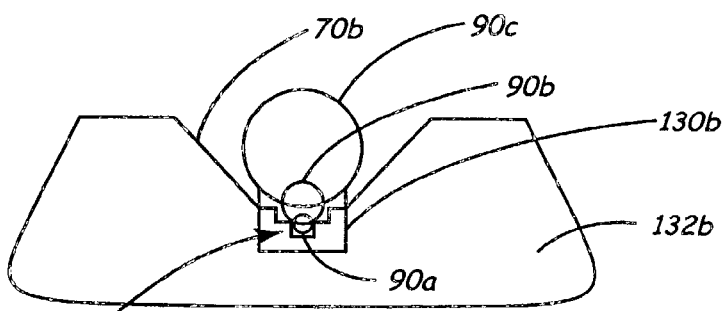
FIG. 14 is yet another cross-sectional view of an embodiment of slitting tool along line 14—14 of FIG. 3.

FIG. 14 is yet another cross-sectional view of an embodiment of slitting tool 50 at line 14—14 of FIG. 3. Recessed area 70b is a shallow "V-shape", with channel 72b being formed by a series of steps that are sized to accommodate IMDs such as leads 90a, 90b, and 90c having varying diameters. A softer overmold area 130b may be provided over the remainder of the slitter body 132b, as previously described. It may be noted that channel 72 may be deeper at the intersection of top surface 52 and front surface 54 than at the location of line 14—14 of FIG. 3. This is evident from comparing FIGS. 12 and 13 to FIGS. 14 and 15. Providing a deeper channel at the top of nose section 53 protects the lead in the manner discussed above.

Figure 15:
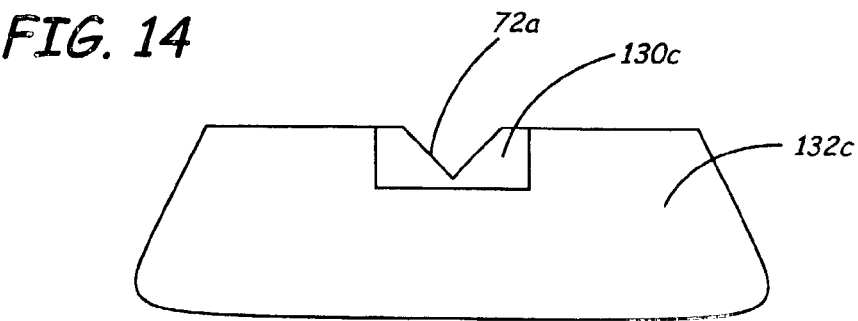
FIG. 15 illustrates an embodiment of slitter without a recessed area along line 14—14 of FIG. 3.

FIG. 15 illustrates an embodiment of slitter without recessed area 70 at line 14—14 of FIG. 3. In this instance, only channel 72c is provided within overmold area 130c. The body 132c of slitter may be provided by a harder material.

Many other configurations for the channel and recessed area may be contemplated. In all instances, these structures are adapted to receive a lead or catheter body without actually providing a clamping structure. The actual retention of the lead or catheter body within the channel is accomplished by the thumb of the user. Because of the flexibility associated with this retention mechanism, the slitting tool of the current invention can be used with lead and/or catheter bodies having different sizes and even different shapes. Thus, various versions of the slitter is generally not needed.

Moreover, the current invention provides an intuitive way to grip and maintain the slitting tool against the lead or catheter body. Instances of misusing the tool in a way that inadvertently damages a lead or catheter are therefore minimized. Finally, because the thumb ensures a fixed relationship between the slitting tool and the lead or catheter body, a user is not inclined to push the slitter against the introducer or guide catheter rather than pull the introducer or guide catheter across the slitter blade. This facilitates proper use of the tool so that lead damage is minimized.

What is claimed is:

1. A slitting tool for use in severing a tubular body positioned around an implantable medical device (IMD), comprising:
   a body member having a top surface and a nose portion coupled to the top surface, the nose portion having a front surface and an inner surface, wherein the front surface and the inner surface define a solid tip portion;
   a gripping mechanism coupled to the body member to be pendent from the body member opposite the top surface;
   the top surface of the body member having an area adapted to receive a thumb when the tool is gripped by a user, the top surface having an open channel to accept an IMD, and whereby gripping action of the thumb of a user maintains the IMD within the channel; and
   a cutting member coupled to the inner surface of the nose section of the body member.

2. The slitting tool of claim 1, wherein the thumb receiving area has a recessed area.

3. The slitting tool of claim 2, wherein the recessed area is textured.

4. The slitting tool of claim 3, wherein the recessed area is surface treated to provide texturing.

5. The slitting tool of claim 4, wherein the recessed area is surface treated using a process selected from the group consisting of plasma etching, chemical milling, and ion bombardment.

6. The slitting tool of claim 1, wherein the body member includes an overmold area formed adjacent a base portion, the overmold area forming at least a portion of the channel.

7. The slitting tool of claim 6, wherein the overmold area is formed of a lower durometer polymer than the base portion of the body member.

8. The slitting tool of claim 7, wherein the lower durometer polymer has a high tack.

9. The slitting tool of claim 1, wherein the gripping mechanism includes a gripping member.

10. The slitting tool of claim 9, wherein the gripping member is a ring to receive at least one finger of a user.

11. The slitting tool of claim 9, wherein the body member includes a guard member to protect the user from the cutting member.

12. The slitting tool of claim 1, wherein a portion of the channel extends adjacent the nose portion.

13. The slitting tool of claim 12, wherein the nose portion is positioned to be placed between the IMD and the tubular body.

14. The slitting tool of claim 1, wherein the cutting member has an angle of less than sixty degrees.

15. The slitting tool of claim 1, wherein the cutting member has a sawtooth edge.

16. The slitting tool of claim 1, wherein the channel includes a textured surface.

17. The slitting tool of claim 16, wherein the channel is surface treated to provide the textured surface.

18. The slitting tool of claim 17, wherein the channel is surface treated using a process selected from the group consisting of plasma etching, chemical milling, and ion bombardment.

19. The slitting tool of claim 1, wherein the channel is adapted to accommodate lead bodies having a diameter of between 2 and 8 French.

20. The slitting tool of claim 1, wherein the channel includes at least one stepped portion to accommodate lead bodies of varying sizes.

21. The slitting tool of claim 12, wherein the channel has a varying depth.

22. The slitting tool of claim 21, wherein the channel is deepest along the portion of the channel extending adjacent the nose portion.

23. The slitting tool of claim 14, wherein the culling member has an angle of between 15 and 45 degrees.

* * * * *